United States Patent [19]
Finch et al.

[11] Patent Number: 6,120,492
[45] Date of Patent: *Sep. 19, 2000

[54] METHOD AND APPARATUS FOR PERCUTANEOUSLY ACCESSING AN IMPLANTED PORT

[75] Inventors: Charles David Finch, Clinton, Miss.; Jeffrey H. Burbank, Boxford; James M. Brugger, Newburyport, both of Mass.

[73] Assignee: Vasca, Inc., Tewksbury, Mass.

[*] Notice: This patent is subject to a terminal disclaimer.

[21] Appl. No.: 09/161,068

[22] Filed: Sep. 25, 1998

Related U.S. Application Data

[63] Continuation-in-part of application No. 08/896,592, Jul. 18, 1997.
[60] Provisional application No. 60/071,241, Jan. 12, 1998.

[51] Int. Cl.[7] .................................................. A61M 31/00
[52] U.S. Cl. ............................ 604/502; 604/264; 604/507
[58] Field of Search ....................................... 604/264, 167, 604/175, 4, 93, 263–265, 502, 506–508, 510, 523, 1–3

[56] References Cited

U.S. PATENT DOCUMENTS

| | | |
|---|---|---|
| 4,181,132 | 1/1980 | Parks . |
| 4,534,759 | 8/1985 | Trawöger . |
| 4,569,675 | 2/1986 | Prosl et al. . |
| 4,634,424 | 1/1987 | O'Boyle . |
| 4,743,231 | 5/1988 | Kay et al. . |
| 5,053,013 | 10/1991 | Ensminger et al. . |
| 5,057,084 | 10/1991 | Ensminger et al. . |
| 5,180,365 | 1/1993 | Ensminger et al. . |
| 5,226,879 | 7/1993 | Ensminger et al. . |
| 5,263,930 | 11/1993 | Ensminger . |
| 5,281,199 | 1/1994 | Ensminger et al. . |
| 5,350,360 | 9/1994 | Ensminger et al. . |
| 5,417,656 | 5/1995 | Ensminger et al. . |
| 5,476,451 | 12/1995 | Ensminger et al. . |
| 5,503,630 | 4/1996 | Ensminger et al. . |
| 5,520,643 | 5/1996 | Ensminger et al. . |
| 5,527,277 | 6/1996 | Ensminger et al. . |
| 5,527,278 | 6/1996 | Ensminger et al. . |
| 5,562,617 | 10/1996 | Finch, Jr. et al. . |
| 5,637,088 | 6/1997 | Wenner et al. . |
| 5,702,363 | 12/1997 | Flaherty . |
| 5,741,228 | 4/1998 | Lambrecht et al. . |
| 5,752,939 | 5/1998 | Makoto . |
| 5,770,193 | 6/1998 | Vacanti et al. . |
| 5,770,417 | 6/1998 | Vacanti et al. . |

FOREIGN PATENT DOCUMENTS

| | | |
|---|---|---|
| T 369268 | 12/1982 | Germany . |
| WO 94/05246 | 3/1994 | WIPO . |
| WO 95/19200 | 7/1995 | WIPO . |
| WO 96/11028 | 4/1996 | WIPO . |
| WO 96/31246 | 10/1996 | WIPO . |
| WO 97/47338 | 12/1997 | WIPO . |
| WO 98/17333 | 4/1998 | WIPO . |

OTHER PUBLICATIONS

Scribner, "The overriding importance of vascular access" *Dial. Transplant.* (1984) 13:652.

Scribner, "Circulatory access—Still a major concern" *Proc. Europ. Dial. Transplant Assoc.* (1982) 19:95–98.

Twardowski et al., "Six–year clinical experience with the creation and use of internal arteriovenous fistulae in patients treated by repeated haemodialyses (translated)" *Pol. Arch. Med. Wewn.* (1977) 57:205–214. An English abstract is included on p. 213 of this publication.

*Primary Examiner*—Wynn Wood Coggins
*Assistant Examiner*—Deborah Blyveis
*Attorney, Agent, or Firm*—Townsend and Townsend and Crew LLP

[57] ABSTRACT

Methods and apparatus for percutaneously accessing an implanted port use an access cannula which is periodically introduced to an aperture on the implanted port so that the cannula passes through the same tissue tract. It has been found that repeated passage of the cannula through the same tissue tract reduces patient trauma, with minimized bleeding, reduction in sensitivity. The tract may be initially formed by percutaneously placing a penetrating element through intact skin to the port and leaving the element in place for a time sufficient to created the tract.

91 Claims, 8 Drawing Sheets

METHOD AND APPARATUS FOR PERCUTANEOUSLY ACCESSING AN IMPLANTED PORT

This application is a continuation-in-part of application Ser. No. 08/896,592, filed on Jul. 18, 1997, and of provisional application No. 60/071,241, filed on Jan. 12, 1998, the full disclosures of which are incorporated herein by reference.

BACKGROUND OF THE INVENTION

1. Filed of the Invention

The present invention relates generally to the design and use of medical devices. More particularly, the present invention relates to a method and apparatus for accessing an implanted port.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications, such as intravenous feeding, intravenous drug delivery, and other applications which continue over only a short time, they are not suitable for hemodialysis, peritoneal dialysis, hemofiltration, and other extracorporeal procedures that must be repeated periodically, often for the lifetime of the patient.

For long-term vascular access suitable for hemodialysis, hemofiltration, and the like, the most common approach is to create a subcutaneous arteriovenous (A-V) fistula. The fistula is preferably created by anastomosing an artery, usually the radial artery, to a vein, usually the cephalic vein. The vein dilates and eventually arterializes, becoming suitable for repeated puncture using a needle for access. A-V fistulas may also be created using autologous or heterologous veins, by implanting synthetic blood vessels, typically PTFE tubes, and the like.

The cannulas used for percutaneously accessing an A-V fistula may be large bore coring needles, often referred to as fistula needles. Alternatively, fistula access may be obtained using a blunt cannula which carries a removable trocar or stylet. In both cases, the cannulas are usually 15 ga. (having a bore diameter of 1.49 mm) or larger, and permit the high blood flow rates needed for hemodialysis, hemofiltration, and other extracorporeal procedures. Usually, the fistula needles or other access cannulas are introduced through a different site on the skin each time the fistula is accessed. By choosing successively different skin access sites, the tissue penetrations to the fistula are allowed to heal.

An alternative technique for repeatedly accessing an A-V fistula is referred to as the "button hole" technique. Such technique relies on repeatedly accessing the fistula through the same tissue tract, eventually creating a channel through the tissue overlying the fistula. The channel is lined with scar tissue which forms over time. While generally successful, the button hole technique results in significant back bleeding from the A-V fistula every time the fistula needle is removed after a treatment is completed. The bleeding, in turn, causes significant clot formation over the length of the tissue tract, and the resulting clot "plugs" must be removed prior to subsequent needle insertion in order to avoid the risk of pushing clot into the fistula. The removal of the clot plug causes patient discomfort and bleeding and increases the risk of infection. More significantly, should the user fail to or incompletely remove the clot plug, portions of the clot can enter circulation and cause embolism. Usually, the access tract to the A-V fistula is at a low angle over a relatively long path, increasing the discomfort, bleeding, and risks of infection and clot embolism.

While the button-hole technique for an A-V fistula can be successful when implemented by skilled personnel, and can result in decreased pain to the patient after the access channel is established, it is a very difficult procedure to learn. In particular, since the user cannot see or feel the entry point on the fistula, proper alignment of the needle to pass precisely through the established tissue tract to reach the same site on the fistula every time is very difficult. Because of the need to repeatedly pass the needle through the established tissue tract, it is recommended that the buttonhole technique be performed by the same "sticker" every time. Usually, this means that the buttonhole technique is only used by home users where the patient or a dedicated assistant can perform the needle stick each time dialysis is performed. As most dialysis is performed in clinics, however, such a requirement greatly limits the utility of the buttonhole technique.

As an alternative to the use of an A-V fistula, a variety of implantable ports have been proposed over the years for use in hemodialysis, hemofiltration, and other extracorporeal treatments. Typically, the port includes a chamber having an access region, such as a septum, where the chamber is attached to an implanted cannula which in turn is secured to a blood vessel. In the case of veins, the cannula is typically indwelling, and in the case of arteries, the cannula may be attached by conventional surgical technique.

Percutaneous access to a port through a septum, however, is generally limited to small diameter, non-coring needles. Large diameter needles will core the septum, i.e. form permanent channels therethrough, which will destroy the septum after repeated uses. Small diameter, non-coring needles will remove little or no material from the septum, allowing it to close after the needle is removed. While small needles will thus preserve the septum, they are generally incompatible with the high flow rates which are used with hemodialysis and other extracorporeal treatments.

Implantable ports having an access aperture and internal valve mechanism for isolating the implanted cannula have also been proposed. One type of implantable valved port is described in a series of issued of U.S. patents which name William Ensminger as inventor. The Ensminger access ports have internal lumens for receiving a percutaneously introduced needle and an internal valve structure for isolating the port from an associated implanted cannula. Generally, the Ensminger ports have a needle-receiving aperture which is oriented at an inclined angle relative to the patient's skin. The Ensminger ports employ relatively large funnel-like entry ports so that needles can be introduced through many different sites in accordance with conventional procedures. The Ensminger patents do not describe port access using large diameter, coring needles, such as fistula needles. Moreover, as many of the specific Ensminger designs employ elastomeric valve elements, it is likely that the valve mechanisms would be damaged if the ports were accessed by a fistula needle or other large bore coring needle. Representative Ensminger patents are listed in the Description of the Background Art below.

Thus far, implantable ports have not found wide spread acceptance in the performance hemodialysis, peritoneal dialysis, or other procedures where large volumes of blood, dialysate, or other fluids are to be exchanged. To the extent implantable ports have been used, it is generally been recommended to move the access site through the skin and/or move the skin relative to the port in order to change the location of the tissue tract between successive access procedures.

For these reasons, it would be desirable to provide improved methods and apparatus for percutaneously accessing a patient's vasculature. Such methods should reduce patient trauma, provide for reliable access to the vasculature, minimize the risk of infection to the patient, and preferably require only minor modifications to present procedures. In particular, it would be desirable to provide methods and apparatus which combine the advantages of the "buttonhole" access technique, such as low pain needle insert and formation of a denervated tissue tract, with the advantages of subcutaneous port access, e.g. reliable performance and low failure rates, high blood and fluid flows through the port with minimum degradation of the blood or other fluid, compatibility with peritoneal dialysis and other non-blood procedures and the ability to utilize an internal valve to provide improved isolation of the blood vessel or other accessed body lumen. Moreover, it would be desirable to overcome certain disadvantages associated with the buttonhole technique when used to access an A-V fistula. For example, it would be desirable if the tissue tract could be formed and accessed by different users so that the procedure could be employed in clinics and other locations where different personnel will treat different patients. Additionally, it would be desirable to reduce the formation of clot from back bleeding into the buttonhole tissue tract and thus lessen the need to remove the clot and reduce the risk of clot emboli. At least some of these objectives will be met by the invention described hereinafter.

2. Description of the Background Art

The "button hole" technique was first described by Dr. Zbylut Twardowski as the "constant site" access method in Twardowski et al. (1977) Pol. Arch. Med. Wewn. 57:205–214 and has been subsequently described in Scribner (1982) Proc. Europ. Dial. Transplant Assoc. 19:95–98 and Scribner (1984) Dial. Transplant 13:652. U.S. Pat. No. 5,562,617 and WO 95/19200, assigned to the assignee of the present application, describe implantable vascular access systems comprising an access port having an internal slit or duck bill valve for preventing back flow into the port. Vascular access ports having various articulating valves for isolating the port from the vascular system in the absence of external percutaneous connection to the port are described in the following U.S. Patents which name William Ensminger as an inventor: U.S. Pat. Nos. 5,527,278; 5,527,277; 5,520,643; 5,503,630; 5,476,451; 5,417,656; 5,350,360; 5,281,199; 5,263,930; 5,226,879; 5,180,365; 5,057,084; and 5,053,013. Other patents and published applications which show implantable ports having valve structures opened by insertion of a needle include U.S. Pat. Nos. 5,741,228; 5,702,363; 4,569,675; 4,534,759; 4,181,132; WO 97/47338; and WO 96/31246. Other patents and published applications relating to peritoneal dialysis include 5,770,417; 5,770,193; 5,752,939; and WO 98/17333. Implantable ports and subcutaneous catheters for connecting the ports for hemodialysis, peritoneal dialysis, and other procedures which are useful in the present invention are described in co-pending application Ser. Nos. 08/539,105; 08/724,948; 09/009,758; 08/942,990; 08/857,386; 08/896,791; 08/856,641; and 09/003,772, the full disclosures of which are incorporated herein by reference.

SUMMARY OF THE INVENTION

The present invention provides improved methods, apparatus, and kits for creating and establishing access to subcutaneously implanted ports for a variety of purposes, including hemodialysis, hemofiltration, hemodiafiltration, apheresis, peritoneal dialysis, drug delivery, and the like. The methods rely at least partly on the surprising discovery that repeated percutaneous penetrations with an access cannula, including but not limited to large bore diameter needles, to a subcutaneously implanted, self-closing access port result in a tissue tract which has minimum back bleeding after the cannula is removed, which rapidly heals even when accessed multiple times in a single day, and which minimizes patient trauma as the tissue tract loses its nerve sensitivity over time. The tissue tracts which result from accessing such implanted ports appear to differ from those which result from accessing an A-V fistula using the so-called "button hole" technique, even when using identical fistula needles.

The tissue tracts created and utilized by the present invention do not result in the same type of tunnel which is developed over time with the "button hole" fistula access technique described above. In particular, the tissue tract formed by the present method will usually have reduced or no clot formation, often eliminating the need to remove a clot plug and significantly reducing the risk of emboli release. It is presently believed that such reduction in clot results at least partly from the ability of a valved or other self-closing port to inhibit bleeding back into the tissue tract when the needle is withdrawn. Inhibition of back bleeding lessens or eliminates clotting and scab formation over the penetration point and through the access tract. The ability to eliminate or lessen scab removal is thus a significant benefit to the patient. In addition, by utilizing the preferred access ports of the present invention, the tissue tract may be formed vertically, thus lessening its length and further reducing bleeding and patient trauma. The access port is also particularly easy to locate beneath the skin, and when combined with the ability to vertically introduce the needle, targeting of the port is greatly simplified. The ability to accurately and simply target the port lessens the chance that the cannula will be misdirected, still further reducing patient trauma and enhancing the unique tissue tract formation which underlies the present invention.

According to a first aspect of the present invention, a method for percutaneously accessing an implanted port in a patient comprises locating a preformed access tract which extends from an entry point on the patient's skin surface to the port. A cannula is percutaneously introduced through the preformed access tract to establish a flow path through the cannula to the port. As described above, over time, repeated percutaneous introductions of the cannula will create a unique tissue tract which becomes lined with scar tissue and has lessened nerve sensitivity, reducing patient trauma as the same tissue tract continues to be used for access. The port will usually have an aperture for receiving the cannula, and the locating step will comprise manually aligning the cannula with a line from the skin entry point (which remains visible on the patient's skin surface) to the aperture on the port, where the aperture can be manually located by feeling the port through the patient's skin and determining the location of the aperture. Usually, the aperture will have dimensions which correspond to those of the cannula, e.g. they will have similar diameters, although in other cases the aperture could comprise a funnel having dimensions substantially larger than the cannula diameter. Usually, however, provision of such a funnel for directing the cannula into the aperture is undesirable since it allows the user to penetrate the cannula through different access tracts.

The cannula may comprise a needle having a sharpened or chamfered distal tip to permit self-penetration of the cannula through the patient's skin. Alternatively, the cannula could comprise a blunt tubular body, optionally including a trocar, stylet, blade, or other sharpened element to assist with self-introduction of the cannula. In some cases, after the access tract is established, it will not be necessary to provide a sharpened element with the cannula in order to assist in percutaneous introduction. That is, a blunt cannula will be able to be passed inwardly through the established tissue tract. Usually, the cannula will have a diameter which is larger than that of the tissue tract which will have collapsed after the cannula was removed in the previous treatment protocol. Thus, as the cannula is introduced through the established tissue tract, the tissue tract will be dilated. Such repeated introduction and dilation of the tissue tract is believed to be part of the treatment method which results in the scar tissue formation and desensitized tissue tract.

In the exemplary embodiments, the cannula will be a large bore cannula, typically having a bore size of at least 1.16 mm (16 gauge), preferably being at least 1.33 mm (15 gauge) and more preferably being at least 1.55 mm (14 gauge) and in some cases being at least 1.73 mm (13 gauge), and in still other cases being at least 2.80 mm (12 gauge). In particular, the cannula may be a large bore fistula or other needle having these dimensions. The needle can be sharp or dull, with the use of sharp needles being presently preferred.

In a second aspect of the present invention, a method for forming a percutaneous access tract to an implanted port comprises percutaneously introducing a cannula to initially define the access tract. The access tract will have a skin entry point and extend to a port, typically to an aperture on the port as generally described above. The access tract is established by repeatedly accessing the port with a cannula (usually different cannulas which may have the same or different geometries, dimensions, and the like) through the same access tract at intervals and over a time period sufficient to cause scar tissue formation over the access tract. Usually, the access intervals and time periods will depend at least in part on the procedures to be performed on the patient. For example, patients undergoing hemodialysis will typically have the cannula introducing step repeated at intervals of at least twice a week, more usually three times a week, for a period of at least three months, usually for indefinite periods. For patients undergoing peritoneal dialysis, the access interval will be much more frequent, usually being at least twice a day, often being at least four times a day, for periods of at least three months, and typically for indefinite periods.

Usually, although not necessarily, the cannula will be introduced in a consistent direction, e.g. generally normal or perpendicular to the skin surface through which it is being introduced, with the repeated access steps eventually creating the nerve depleted tissue tract described above.

In a third aspect of the present invention, a method for creating an access tract at the time a port is initially implanted comprises implanting the port in a subcutaneous tissue pocket where an access cannula-receiving aperture of the port is disposed beneath an intact region of the skin. This is usually accomplished by creating an initial surgical incision which is laterally offset from the main portion of the tissue pocket so that the port may be disposed under skin which has not been surgically penetrated. After the port is in place, a penetrating element may be introduced through the intact region of skin and into the port aperture. The penetrating element, which may be a rod, tube, or preferably access cannula of the type used for subsequent access to the port, will be left in place and remain anchored in the aperture for a time sufficient to create the access tract, usually for at least about one week, more usually for a least about two weeks, and until sufficient healing has occurred around the penetrating element to leave an access tract for subsequent cannula introduction. A particular advantage of this method for creating the access tract is that the tract will be formed simultaneously with healing of the surgical introduction of the port and associated subcutaneous cannula. A further advantage, when an access cannula is used as the penetrating element, is that fluids may be introduced and removed from the port during the healing period.

In yet another aspect of the method of the present invention, access cannulas may be aligned with a preformed tissue tract by visually observing the patient's skin to locate an access site. The access site will be at the proximal end of the preformed tissue tract and will be visually apparent, usually as a small hole or other mark on the skin. Prior to introducing the access cannula, the cannula will be both aligned with the access site and positioned so that it will be in coaxial alignment with the known direction of the tissue tract. In the case of the exemplary subcutaneous ports described hereinafter, the direction will be generally vertical or normal to the patient's skin in the region of the access site. Thus, before the access cannula is actually introduced, it will be at the proper orientation so that it will pass through the preformed access tract with minimum discomfort and trauma.

The present invention still further provides kits comprising a cannula, often a large bore cannula having a bore size of at least about 1.16 mm (16 G), such as a fistula needle or blunt cannula with a trocar or stylet. The kit further comprises instructions for use setting forth any of the methods described above. The needle and the instructions for use are packaged together, where the instructions may be on a separate instruction sheet and/or may be provided on a portion of the packaging. Usually, the cannula will be part of a catheter, where the needle is connected or connectable to the catheter to provide a flow path through the needle and into a lumen of the catheter. Kits according the present invention may also comprise an implantable port together with instructions for use setting forth any of the methods described above for implanting the port and creating a cannula access tract to the port. The port and the instructions for use will typically be packaged together, using any of the packages described hereinafter, and other kit components, such as a penetrating element, access cannula, or the like, may also be provided.

DESCRIPTION OF THE SPECIFIC EMBODIMENTS

Figure 1:
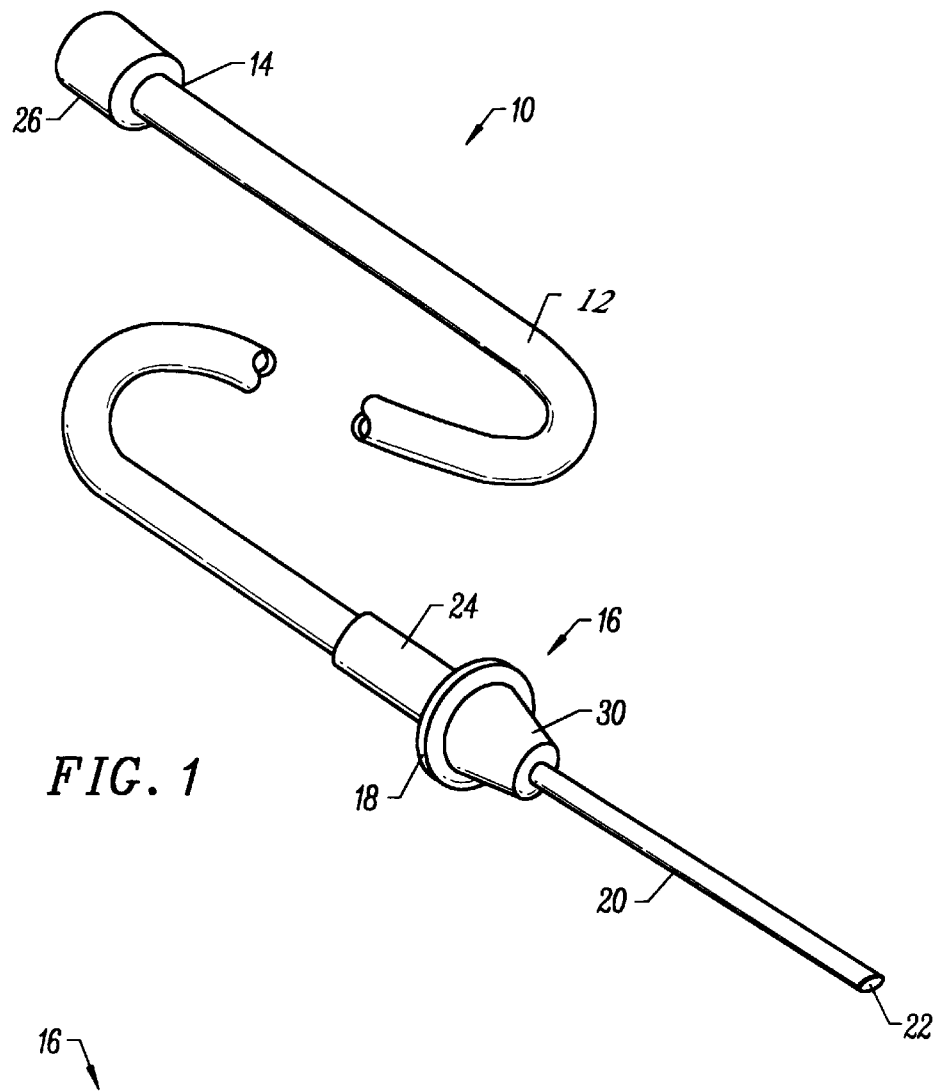
FIG. 1 is a perspective view of a first embodiment of an access catheter having a large diameter needle suitable for use in the methods and kits of the present invention.

The methods and apparatus of the present invention for creating and using a percutaneous access tract are useful with virtually any type of implantable access port having an aperture capable of receiving a cannula, including but not limited to large bore cannulas, such as fistula needles. The methods of the present invention may be performed with implantable ports having one, two, three, or more, discrete access ports which may be vertically or otherwise repeatedly aligned with the access tract to be percutaneously formed through overlying tissue. Such access tracts will be useful for repeated access to the aperture, where the aperture defines a specific target site through the overlying tissue.

The preferred access ports will have at least one aperture which removably receives the access cannula, optionally in a vertical orientation in order to minimize distance of the tissue tract. The access port will preferably be capable of immobilizing the access needle while the blood is being transferred through the port. Exemplary access ports are described in co-pending application Ser. No. 08/942,990, filed on Oct. 2, 1997, which was a continuation in part of application Ser. No. 60/036,124, which has previously been incorporated herein by reference. Typically, the port will be implanted beneath the skin by a distance in the range from about 3 mm to 20 mm, usually from 5 mm to 15 mm.

The access cannulas utilized in the methods, apparatus, and kits of the present invention may comprise any of a variety of hollow bore needles, tubes, or the like, which are capable of being percutaneously introduced to the previously implanted port. Usually, the cannulas will comprise a sharpened distal tip, (in which case they are often referred to as needles) or a separate element which may be removably placed in the cannula to provide such a sharpened distal end. Such elements may comprise stylets, trocars, blades, or the like. In some instances, the tips of the separate elements may have diameters which are larger than the diameter of the cannula itself. For example, blades having a width larger than the cannula diameter may be placed through the cannula using a rod in order to cut a path as the assembly of the cannula and blade is advanced through the tissue tract. In such instances, the blade will usually be sufficiently flexible so that it may later be collapsed and withdrawn proximally through the cannula in order to provide clear access through the cannula lumen to the port. Cannulas having sharpened distal tips or separate elements having sharpened distal ends will usually be used at least for the initial percutaneous access steps which the tissue tract is being formed. After the tissue tract is established, i.e. sufficient scar tissue is formed along the tissue tract to maintain the tract between successive access steps with the cannulas, is not always necessary to provide a sharpened tip on the cannula or separate element. In those instances, a blunt cannula or tube can be introduced through the tissue tract. Often, however, it will still be preferred to use a cannula having a sharpened tip or separate element to facilitate such introduction.

An exemplary embodiment of the present invention utilizes large bore coring needle, such as conventional fistula needle. By "coring needles," it is meant that the distal tip of the needle will be sharpened and will be open in a forwardly direction so that the needle is capable of cutting tissue (and coring septums) as it is advanced therethrough in a forwardly direction. It is also possible to use in the present invention are needles having a non-coring design, such as Huber needles which have a side-facing distal opening as well as stylets, etc. The preferred needles and other cannulas will have a bore size of at least 1.16 mm (16 G), usually at least 1.33 mm (15 G), more usually at least 1.55 mm (14 G), still more usually at least 1.73 mm (13 G), and sometimes as large as 2.08 mm (12 G), or larger. The needles may be composed of any conventional needle material, typically being a stainless steel, but could also be hard plastic.

In preferred embodiments, the access needle will be incorporated into a catheter, as described in co-pending application Ser. No. 08/896,790, or into a peritoneal dialysis tubing set, as described in co-pending application Ser. No. 08/896,791, the full disclosures of which have been previously incorporated herein by reference. Such catheters incorporating the access needle will now be described in detail together with methods for their use according to the present invention.

Figure 2:
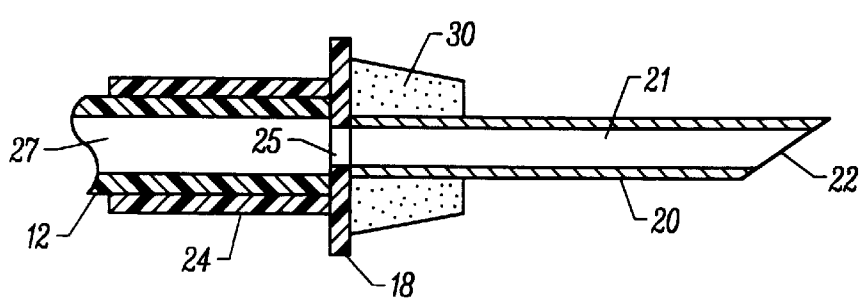
FIG. 2 is a detailed view of the distal end of the catheter of FIG. 1, showing the access needle in cross-section.

Referring now to FIGS. 1 and 2, an access catheter 10 incorporating a large bore coring needle 20 in accordance with the principles of the present invention will be described. The catheter 10 comprises a catheter body 12 having a proximal end 14 and a distal end 16. The catheter body 12 will typically comprise a flexible polymer tube, composed of a medically compatible organic polymer, such as polyvinylchloride, and having a length in the range from 10 cm to 30 cm, preferably from 12 cm to 18 cm, and a lumenal diameter in the range from 1 mm to 5 mm, usually from 3.4 mm to 4.6 mm. Such polymeric tubes may be formed by extrusion and will typically include a single lumen extending the entire length from the proximal end 14 to the distal end 16.

Fitting 18 is secured to the distal end of catheter body 12, typically by an adhesive, heat welding, solvent bonding, penetrating fasteners (not shown), or other conventional means. The fitting is shown as a generally flat disk but could have a variety of alternative geometries. The access tube 20 is secured to the distally forward face of the disk, and the lumen of the needle is fluidly coupled to and aligned with the lumen of catheter body 12. An orifice 25 is disposed in the disk 18 and generally aligned between the lumen 21 of the needle, thus opening into lumen 27 in the catheter body. Usually, a connector 26, such as a luer connector, is provided at the proximal end 14 of the catheter body 12. Such a connector, however, is not necessary and it is possible to directly connect the catheter body to a desired treatment device, fluid source, or other external apparatus.

As described in detail in co-pending application Ser. No. 08/896,790, a compressible element 30 is attached at the distal end 16 of the catheter body 12. Preferably, the compressible element is coaxially disposed about the proximal end of needle 20. The compressible element 30 may be impregnated with an antiseptic, antibiotic, or other active agent, which can be delivered to the skin's surface as the needle 20 is penetrated therethrough. Such a compressible element, although generally preferred for use in combination with the needles of the present invention, does not form part of the present invention.

Figure 3:
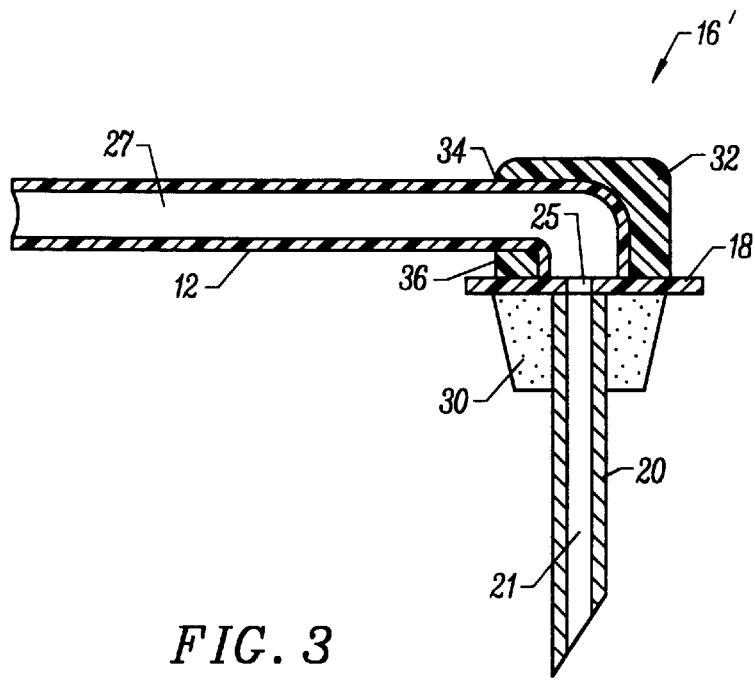
FIG. 3 is a detailed view of an alternative distal end of the catheter of FIG. 1, showing the access needle in cross-section.

Referring now to FIG. 3, an alternative configuration 16' of the distal end of the catheter 10 orients the access needle 20 at an approximately right angle (90°) relative to the distal end of the catheter body 12. The fitting 18 includes cap 32 which defines the 90° bend with an inlet 34 receiving the distal end of the catheter body 12 and an outlet 36 connected to the fitting 18. The catheter body 12 can extend through the internal passage of cap 32 or, alternatively, may be secured at the inlet end. In either case, the substantially continuous lumen 27 is created through the catheter body to the orifice 25 and fitting 18 and thus to the lumen 21 of access needle 20.

Figure 3A:
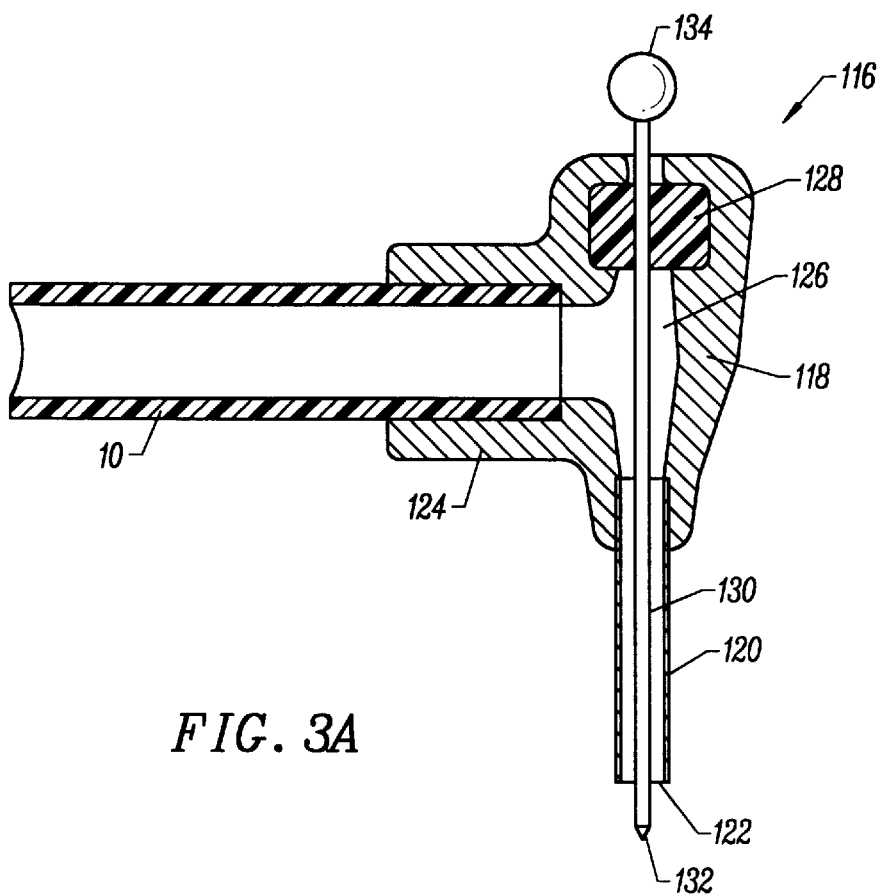
FIG. 3A is a detailed view of a distal end of an alternative access cannula which may be utilized in the methods and kits of the present invention.

Referring now to FIG. 3A, a second alternative configuration 116 of the distal end of the catheter 10 orients an access cannula 120 having a blunt distal end 122 at an approximately right angle (90°) relative to the distal end of the catheter 10. A fitting 118 receives the catheter 10 in a nipple 124 which aligned at a right angle relative to a vertical passage 126. A penetrable seal 128 is positioned at the upper end of the passage 118 and permits removable entry of a stylet 130 having a sharpened distal end 132 which extends through the blunt end 122 of cannula 120. The stylet includes a handle 134 at its proximal end to permit removal the stylet after the cannula 120 has been introduced through a tissue tract to an implanted port. The sharpened tip 132 of the stylet may take any of the forms discussed above, including a conical taper, a chamfered taper, a widened blade, or any other configuration which facilitates penetration of the assembly of the cannula 120 and stylet 130 through skin as the cannula is advanced toward the implanted port. The dimensions of the cannula 120 will usually but not necessarily be within the ranges set forth above.

Figure 4A:
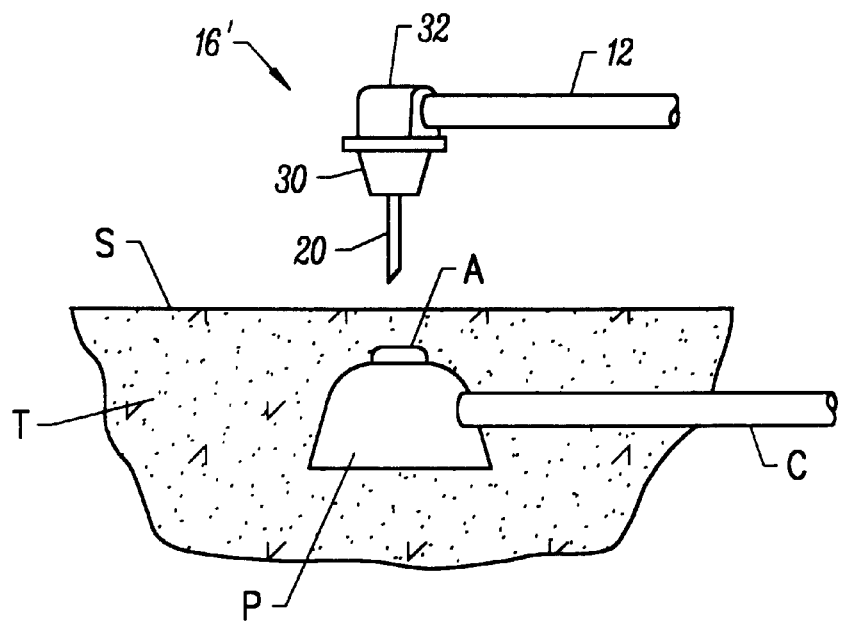
FIGS. 4A–4D illustrate use of the access needle and catheter of FIGS. 1–3 for creating and accessing a subcutaneously implanted port according to the methods of the present invention.
Figure 4B:
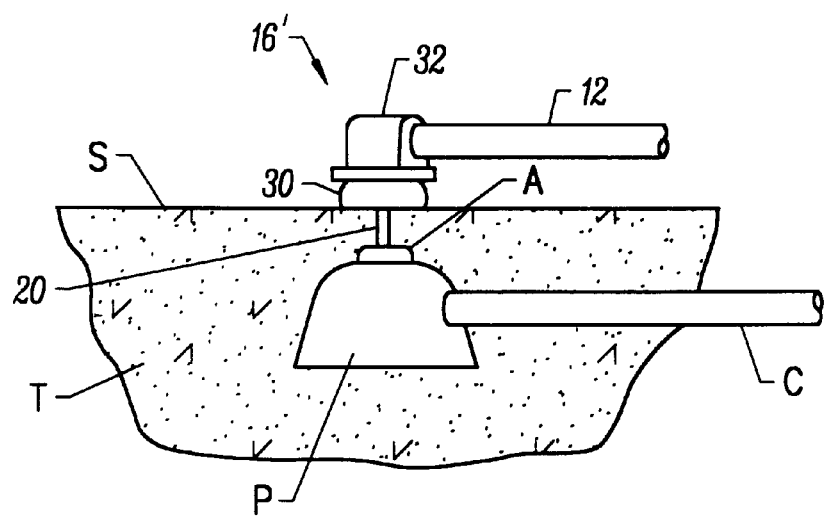

Referring now to FIGS. 4A–4D, use of the catheter 10 having the distal end 16' (FIG. 3) and access needle 20 for creating an access tract and accessing an implanted port P through the access tract will be described. The port P will have an aperture A which is preferably oriented to receive a vertically aligned needle. That is, the access needle 20 will preferably be percutaneously introduced through the skin surface S in a direction which is normal to or perpendicular to the plane of the skin at the point where the needle is being introduced. While vertical access is preferred and may be accomplished using the exemplary ports of the present invention, percutaneous access according to the present invention may also be achieved used non-vertical access direction, i.e. where access is accomplished by penetrating a needle or other device at a relatively low angle relative to the skin, often between 15° and 45° relative to the skin surface. After entering the port P, the access needle 20 will actuate an internal valve (not shown) to open a flow path with a lumen and cannula C, where the cannula may be connected to a blood vessel or other body lumen or cavity, as described in detail in co-pending application Ser. No. 08/856,641, filed on May 15, 1997. The present invention is useful with a variety of other valved and non-valved access ports. For example, it will be useful with valved access ports of the type described in the Ensminger patents listed above, as well as ports described in issued U.S. Pat. Nos. 5,741,228; 5,702,363; 4,569,675; 4,534,795; 4,181,132; and published PCT applications WO 97/47338 and WO 96/31246, the full disclosures of which are incorporated herein by reference. While the use of valved ports which provide for positive shutoff and isolation of the attached body lumen, and in particular provide for complete cessation of back bleeding when an access cannula is removed from ports attached to blood vessels, the present invention may also find use with other self-sealing ports, such as septum ports, a number of which are described in the patents listed in the Background section of the application. The access needle 20 may be aligned over the aperture A by manually feeling the top of the port P. The port P is generally symmetric with the aperture positioned in the center of the port. The user can feel the periphery of the port P and visually determine its center. The needle 20 is then vertically penetrated through the skin and into the aperture, as shown in FIG. 4B. The thickness of tissue T overlying the aperture is generally from 3 mm to 15 mm, as described above.

Figure 4C:
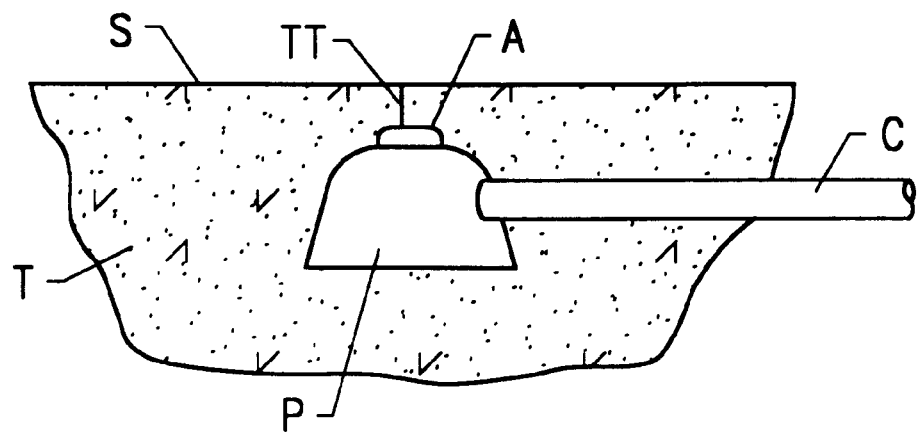

The needle 20 will be left in place in port P while the desired procedure, such as hemodialysis, hemofiltration, peritoneal dialysis, or other procedure, is performed and completed. After completion of the procedure, the needle 20 will be withdrawn, as illustrated in FIG. 4C. Withdrawal of the needle will leave a tissue tract TT through the tissue T overlying the port P. Because the internal valve of port P will have closed, bleeding from the body lumen, typically a blood vessel, will be inhibited. Both the vertical orientation of needle entry and the inhibition of back bleeding into the tissue tract which is left after withdrawal of the needle contribute to the lessening or elimination of scab formation and reduction in patient trauma and rapid healing. Surprisingly, such benefits may be achieved even when using the preferred large bore access needles described above. The rapid healing and minimum trauma have been found even when the port is accessed as many as four times per day. Such a result could not have been predicted prior to the present invention and provides substantial advantages over the use of the non-coring needles typically used with implanted ports, where the user is instructed not to puncture the needle in the same location twice in succession.

Figure 4D:
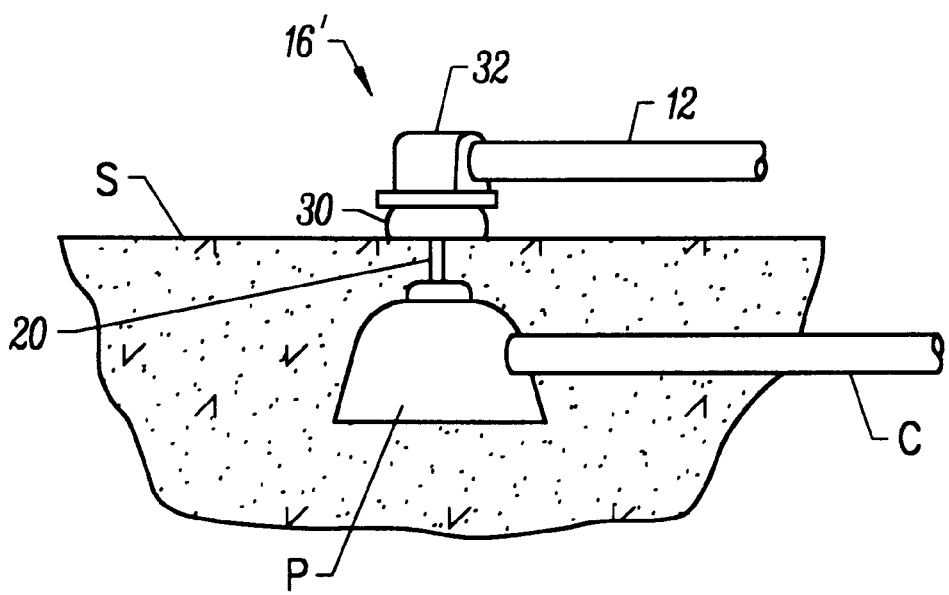

The tissue tract remaining after withdrawal of the catheter, as shown in FIG. 4C, is ready to receive a second catheter as shown in FIG. 4D virtually immediately after the first catheter is withdrawn. Typically, additional access needles 20 and associated catheters will be introduced over periods of from two hours to four days, usually from four hours to two days. Such cycle times are suitable for performing a wide variety of chronic procedures, such as hemodialysis, hemofiltration, peritoneal dialysis, and the like.

Figure 4E:
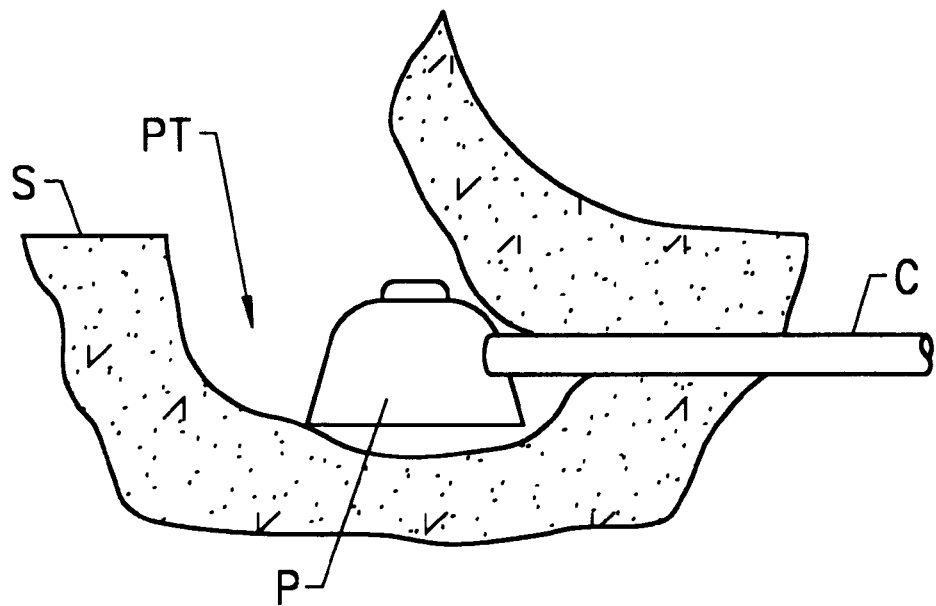
FIGS. 4E—4G illustrate an alternative technique for creating and accessing a subcutaneously implanted port according to the methods of the present invention.
Figure 4F:
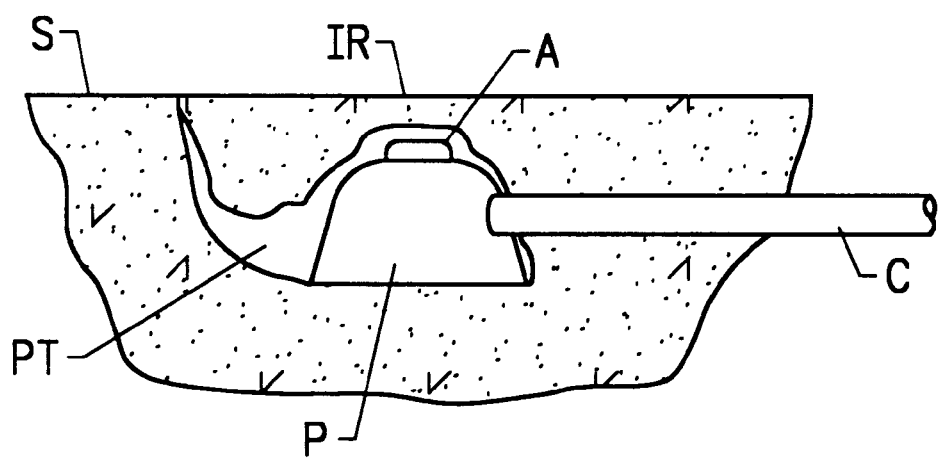
Figure 4G:
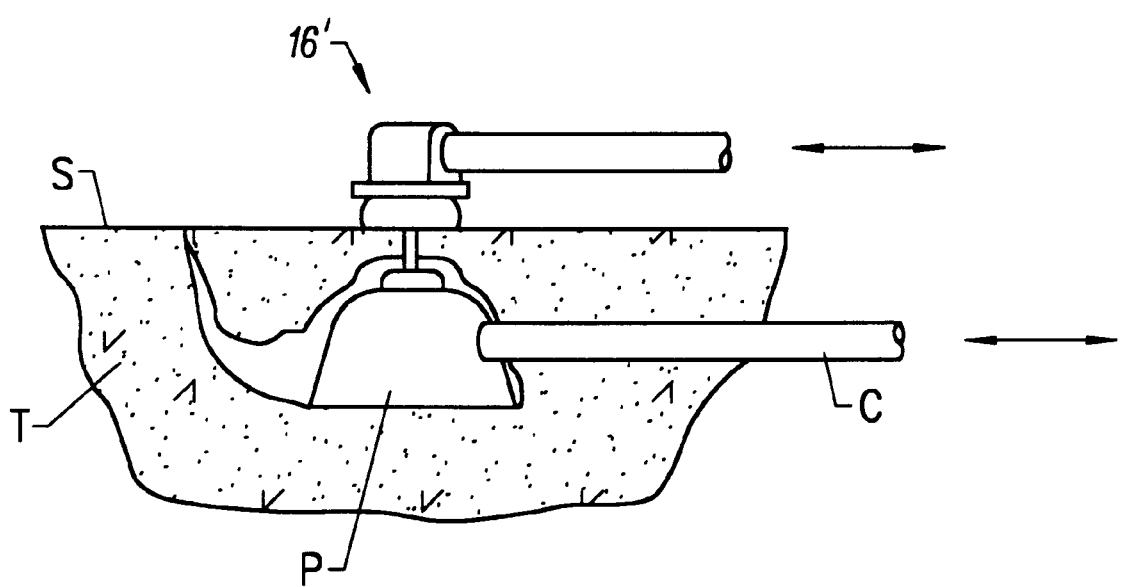

As just described, the tissue tract of the present invention may be established at any time after a port has been subcutaneously implanted. In many instances, it will be desirable to begin creating the tissue tract at the time the port is initially implanted. Referring to FIGS. 4E–4G, a port P, which may be any of the valved or non-valved ports described above, is implanted by creating a tissue pocket PT by making an incision in the skin S and forming the pocket laterally from the incision. The port P may then be placed in the pocket PT and connected to a cannula in any manner. After the tissue pocket PT is closed, as shown in FIG. 4F, an intact region of skin IR will overlay the access cannula target aperture A. A tissue penetrating element, which may be a needle, rod, stylet, tube, or virtually any other penetrating element, may then be introduced through the intact region of skin IR, as shown in FIG. 4G. In FIG. 4G, an access cannula 16' is used as the penetrating element, but it will be appreciated that this is not necessary for initial tissue tract formation. It is preferable, however, since use of an access cannula permits blood or other fluids to be exchanged through the implanted port from a time very shortly after implantation of the port. The penetrating element will be left in place transcutaneously through the skin for a time sufficient to at least begin forming the tissue tract, usually for at least one week, preferably for at least two weeks. After that initial time, the tissue penetrating element may be removed and the resulting tissue tract accessed using access cannulas according to the method of the present invention described above. Continued accessing of the port P through the preformed tissue tract will continue to cause scarring and denervation of the tissue tract, further establishing and defining the tissue tract over time.

Figure 5:
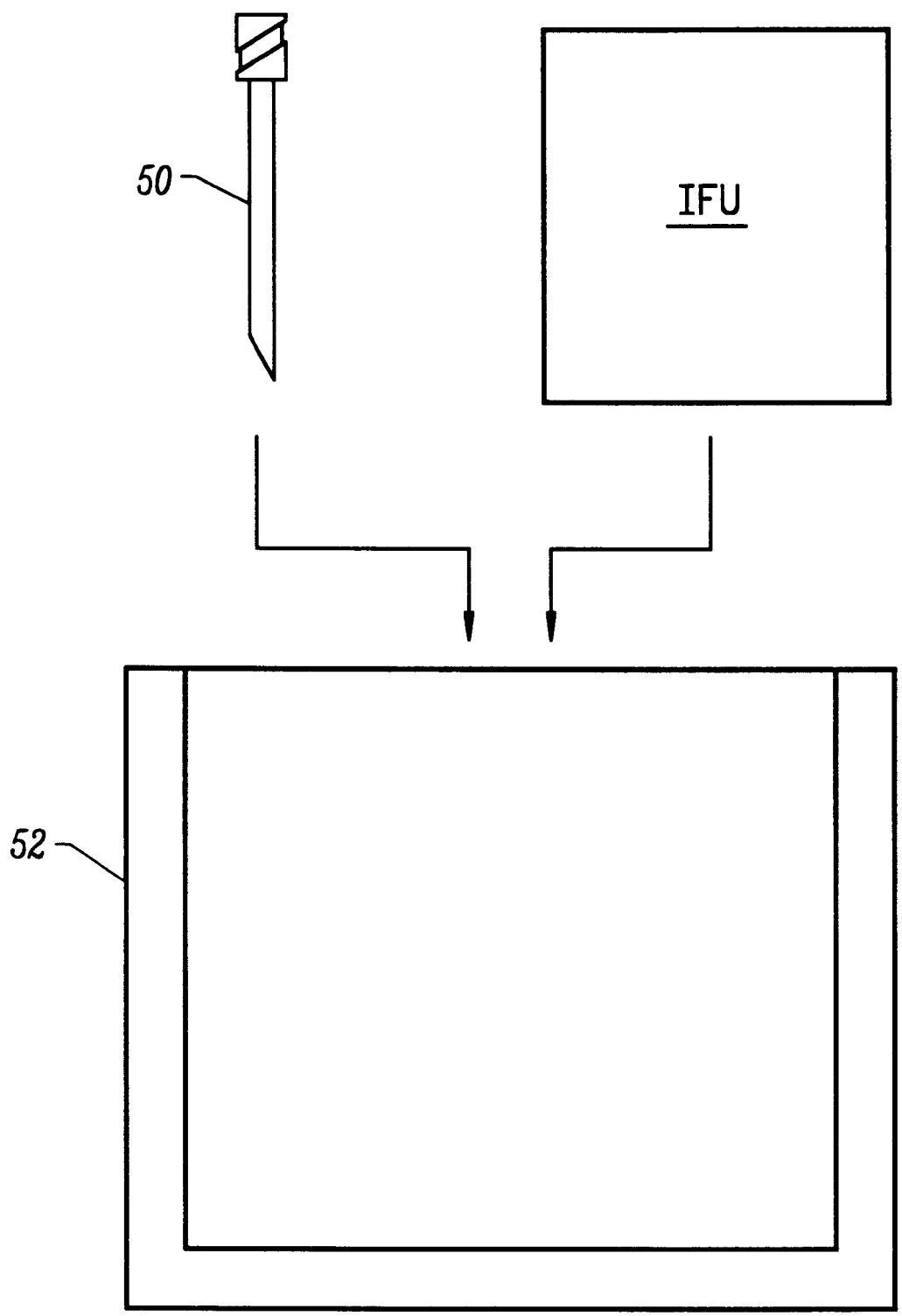
FIG. 5 illustrates a kit according to the present invention comprising a large bore coring needle, a package, and instructions for use.

Referring now to FIG. 5, a needle 50, typically but not necessarily a large bore coring needle, according to the present invention, may be packaged together with instructions for use (IFU) in a kit, as shown in FIG. 5. A conventional package which may be a pouch 52 or any other suitable package, such as a tray, box, tube, or the like, may be used to contain the needle 50 and the IFU, where the IFU may be printed on a separate sheet and/or may be printed on the packaging itself. Optionally, but not necessarily, the needle may be sterilized within the package, e.g. by radiation, steam, or ethyleneoxide. The instructions may set forth any of the aspects of the method of the present invention described above.

Figure 6:
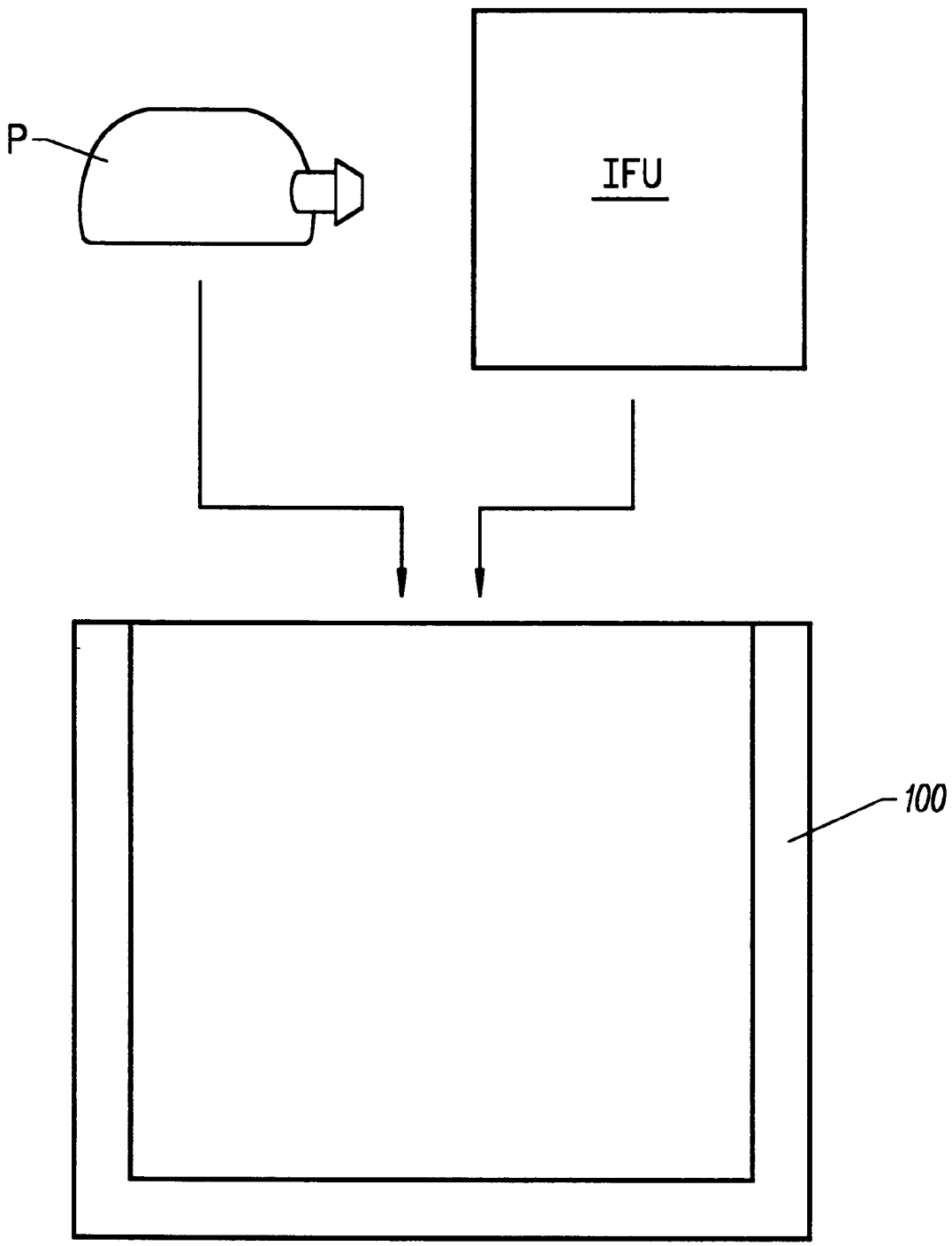
FIG. 6 illustrates a kit according to the present invention comprising a subcutaneously implantable port, a package, and instructions for use describing how to create an access tract according to the present invention.

Referring now to FIG. 6, a port P may be packaged together with instructions for use (IFU) in a kit. A conventional package 100, which may be in the form of a pouch, tray, box, tube, or the like, may be used to contain both the port and the instructions for use. Additional kit components, such as a penetrating element, access cannula, or the like, may also be included in the kit. Optionally, but not necessarily, all kits components may be sterilized within the package, and the instructions for use may be set forth on a separate sheet of paper and/or on the packaging itself. The instructions may set forth any of the aspects of the method of the present invention for implanting the port or subsequently accessing the port using an access cannula as described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for percutaneously accessing an implanted port, said method comprising:
   locating a preformed access tract from a skin entry point to the port; and
   percutaneously introducing a cannula through the preformed access tract to establish a flow path through the cannula to the port, wherein the port has an internal valve that inhibits bleed back into the tissue tract after the cannula is withdrawn.

2. A method as in claim 1, wherein the port comprises an aperture and the locating step comprises manually aligning the cannula with a line from the skin entry point of the access tract to the aperture on the port.

3. A method as in claim 2, wherein the aperture has dimensions which correspond to the cannula.

4. A method as in claim 2, wherein the locating step further comprise annularly feeling the port to determine the position of the aperture.

5. A method as in claim 1, wherein the introducing step comprises orienting the cannula generally vertically with respect to the skin surface.

6. A method as in claim 1, wherein the cannula is introduced through a skin layer having a thickness in the range from 3 mm to 20 mm.

7. A method as in claim 1, wherein the cannula dilates the access tract as it is introduced therethrough.

8. A method as in claim 7, wherein the cannula has a bore size of at least 1.16 mm.

9. A method as in claim 1, wherein the cannula comprises a needle.

10. A method as in claim 1, wherein the cannula comprises a blunt tube.

11. A method as in claim 10, wherein the cannula further comprises a stylet removably received in the blunt tube.

12. A method for forming a percutaneous access tract to an implanted port, said method comprising:
   percutaneous introducing a cannula to define an access tract having a skin entry point and extending to the port; and
   repeatedly accessing the port with a cannula through the same access tract at intervals of at least twice a week for a period of at least three months.

13. A method as in claim 12, wherein the accessing step comprises introducing a cannula at intervals of at least twice a day for a period of at least three months.

14. A method as in claim 12, wherein the introducing step comprises orienting the cannula generally vertically with respect to the skin surface.

15. A method as in claim 12, wherein the cannula is introduced through a skin layer having a thickness in the range from 3 mm to 20 mm.

16. A method as in claim 12, wherein the port has an internal valve that inhibits bleed back into the tissue tract after the cannula is withdrawn.

17. A method as in claim 12, wherein the cannula dilates the access tract as it is introduced therethrough.

18. A method as in claim 17, wherein the cannula has a bore size of at least 1.16 mm.

19. A method as in claim 12, wherein the cannula comprises a needle.

20. A method as in claim 12, wherein the cannula comprises a blunt tube.

21. A method as in claim 20, wherein the cannula further comprises a stylet removably received in the blunt tube.

22. A method for aligning an access cannula, said method comprising:
   observing an access site on skin at the proximal end of a preformed access tract, wherein said access site overlies an implanted port capable of removably receiving the access cannula through the access tract having an internal valve that inhibits bleed back into the tissue tract after the access tube is removed; and
   aligning an access cannula with the access site and at an angle coaxial with that of the access tract.

23. A method as in claim 22, wherein the angle is generally normal relative to the patients skin at the access site.

24. A kit comprising:
   a cannula;
   instructions for use setting forth a method according to claim 1; and
   a package containing the cannula and the instructions for use.

25. A kit as in claim 24, further comprising a catheter connected or connectable to the cannula.

26. A kit comprising:
   a cannula;
   instructions for use setting forth a method according to claim 12; and
   a package containing the cannula and the instructions for use.

27. A kit as in claim 26, further comprising a catheter connected or connectable to the cannula.

28. A method comprising (1) advancing and inserting an access cannula into an implantable vascular or peritoneal access port to gain access to the port while simultaneously opening a closure valve of said port which is normally biased closed; (2) exchanging fluid between said cannula and said port; and (3) withdrawing said needle from the port and allowing said valve to close;

characterized in that steps 1 to 3 are repeated with the cannula travelling along the same access tract.

29. The method of use of an implantable access port having an actuatable valve biased in a closed position wherein access cannulas repeatedly access said port along the same access tract, in a therapeutic process wherein the port is connected to a blood vessel and the process comprises removing blood through a port from a patient, processing said blood, and returning the blood through a port to the patient.

30. The method of use of an implantable access port having an actuatable valve biased in a closed position wherein access cannulas repeatedly access said port along the same access tract, in a therapeutic process wherein the port is connected to the peritoneum and the process comprises introducing dialysate to the patient through the port and thereafter removing dialysate from the patient through the port.

31. A method for percutaneously accessing an implanted port having an aperture, said method comprising:

locating a preformed access tract from a skin entry point to the port;

annularly feeling the port to determine the position of the aperture;

manually aligning the cannula with a line from the skin entry point of the access tract to the aperture on the port; and percutaneously introducing a cannula through the preformed access tract into the aperture to establish a flow path through the cannula to the port.

32. A method as in claim 31, wherein the aperture has dimensions which correspond to the cannula.

33. A method as in claim 31, wherein the introducing step comprises orienting the cannula generally vertically with respect to the skin surface.

34. A method as in claim 31, wherein the cannula is introduced through a skin layer having a thickness in the range from 3 mm to 20 mm.

35. A method as in claim 31, wherein the port has an internal valve that inhibits bleed back into the tissue tract after the cannula is withdrawn.

36. A method as in claim 34, wherein the cannula dilates the access tract as it is introduced therethrough.

37. A method as in claim 36, wherein the cannula has a bore size of at least 1.16 mm.

38. A method as in claim 34, wherein the cannula comprises a needle.

39. A method as in claim 34, wherein the cannula comprises a blunt tube.

40. A method as in claim 34, wherein the cannula further comprises a stylet removably received in the blunt tube.

41. A method for forming a percutaneous access tract to an implanted port, said method comprising:

percutaneous introducing a cannula to define an access tract having a skin entry point and extending to the port, wherein the port has an internal valve that inhibits bleed back into the tissue tract after the cannula is withdrawn; and repeatedly accessing the port with a cannula through the same access tract at intervals and over a time period sufficient to cause scar tissue formation over the access tract.

42. A method as in claim 41, wherein the accessing step comprises introducing a cannula at intervals of at least twice a week for a period of at least three months.

43. A method as in claim 41, wherein the accessing step comprises introducing a cannula at intervals of at least twice a day for a period of at least three months.

44. A method as in claim 41, wherein the introducing step comprises orienting the cannula generally vertically with respect to the skin surface.

45. A method as in claim 41, wherein the cannula is introduced through a skin layer having a thickness in the range from 3 mm to 20 mm.

46. A method as in claim 41, wherein the cannula dilates the access tract as it is introduced therethrough.

47. A method as in claim 46, wherein the cannula has a bore size of at least 1.16 mm.

48. A method as in claim 41, wherein the cannula comprises a needle.

49. A method as in claim 41, wherein the cannula comprises a blunt tube.

50. A method as in claim 49, wherein the cannula further comprises a stylet removably received in the blunt tube.

51. A method for creating an access tract to a subcutaneously implanted port, said method comprising:

implanting a port in a subcutaneous tissue pocket, wherein an access cannula-receiving aperture of the port is disposed beneath an intact region of skin; and introducing a penetrating element through the intact region of skin into the aperture, wherein the element remains anchored in the aperture for at least one week.

52. A method as in claim 51, wherein the penetrating element is an access cannula, said method further comprising introducing or removing fluids through the access cannula while said cannula remains anchored in the aperture.

53. A kit comprising:

a cannula;

instructions for use setting forth a method according to claim 31; and a package containing the cannula and the instructions for use.

54. A kit as in claim 52, further comprising a catheter connected or connectable to the cannula.

55. A kit comprising:

a cannula;

instructions for use setting forth a method according to claim 41; and a package containing the cannula and the instructions for use.

56. A kit as in further comprising a catheter connected or connectable to the cannula.

57. A kit comprising:

a subcutaneously implantable port;

instructions for implanting the port in accordance with the method of claim 51; and a package containing the port and the instructions for use.

58. A kit as in claim 57, further comprising a penetrating element.

59. A kit as in claim 53, wherein the penetrating element comprises an access cannula.

60. A method for percutaneously accessing an implanted port, said method comprising:

locating a preformed access tract from a skin entry point to the port; and percutaneously introducing a cannula through the preformed access tract to establish a flow path through the cannula to the port, wherein the cannula has a bore size of at least 1.16 mm and dilates the access tract as it is introduced therethrough.

61. A method as in claim 55, wherein the port comprises an aperture and the locating step comprises manually aligning the cannula with a line from the skin entry point of the access tract to the aperture on the port.

62. A method as in claim 61, wherein the aperture has dimensions which correspond to the cannula.

63. A method as in claim 61, wherein the locating step further comprise annularly feeling the port to determine the position of the aperture.

64. A method as in claim 55, wherein the introducing step comprises orienting the cannula generally vertically with respect to the skin surface.

65. A method as in claim 55, wherein the cannula is introduced through a skin layer having a thickness in the range from 3 mm to 20 mm.

66. A method as in claim 55, wherein the port has an internal valve that inhibits bleed back into the tissue tract after the cannula is withdrawn.

67. A method as in claim 55, wherein the cannula comprises a needle.

68. A method as in claim 55, wherein the cannula comprises a blunt tube.

69. A method as in claim 68, wherein the cannula further comprises a stylet removably received in the blunt tube.

70. A method for forming a percutaneous access tract to an implanted port, said method comprising:
   percutaneous introducing a cannula to define an access tract having a skin entry point and extending to the port, wherein the cannula has a bore size of at least 1.16 mm and dilates the access tract as it is introduced therethrough; and
   repeatedly accessing the port with a cannula through the same access tract at intervals and over a time period sufficient to cause scar tissue formation over the access tract.

71. A method as in claim 70, wherein the accessing step comprises introducing a cannula at intervals of at least twice a week for a period of at least three months.

72. A method as in claim 70, wherein the accessing step comprises introducing a cannula at intervals of at least twice a day for a period of at least three months.

73. A method as in claim 70, wherein the introducing step comprises orienting the cannula generally vertically with respect to the skin surface.

74. A method as in claim 70, wherein the cannula is introduced through a skin layer having a thickness in the range from 3 mm to 20 mm.

75. A method as in claim 70, wherein the port has an internal valve that inhibits bleed back into the tissue tract after the cannula is withdrawn.

76. A method as in claim 70, wherein the cannula comprises a needle.

77. A method as in claim 70, wherein the cannula comprises a blunt tube.

78. A method as in claim 77, wherein the cannula further comprises a stylet removably received in the blunt tube.

79. A kit comprising:
   a cannula;
   instructions for use setting forth a method according to claim 60; and
   a package containing the cannula and the instructions for use.

80. A kit as in claim 79, further comprising a catheter connected or connectable to the cannula.

81. A kit comprising:
   a cannula;
   instructions for use setting forth a method according to claim 70; and
   a package containing the cannula and the instructions for use.

82. A kit as in claim 81, further comprising a catheter connected or connectable to the cannula.

83. A method for percutaneously accessing an implanted port, said method comprising:
   locating a preformed access tract from a skin entry point to the port; and
   percutaneously introducing a cannula comprising a blunt tube having a stylet removably received therein through the preformed access tract to establish a flow path through the cannula to the port.

84. A method as in claim 83, wherein the port comprises an aperture and the locating step comprises manually aligning the cannula with a line from the skin entry point of the access tract to the aperture on the port.

85. A method as in claim 84, wherein the aperture has dimensions which correspond to the cannula.

86. A method as in claim 84, wherein the locating step further comprise annularly feeling the port to determine the position of the aperture.

87. A method as in claim 83, wherein the introducing step comprises orienting the cannula generally vertically with respect to the skin surface.

88. A method as in claim 83, wherein the cannula is introduced through a skin layer having a thickness in the range from 3 mm to 20 mm.

89. A method as in claim 83, wherein the port has an internal valve that inhibits bleed back into the tissue tract after the cannula is withdrawn.

90. A method as in claim 83, wherein the cannula dilates the access tract as it is introduced therethrough.

91. A method as in claim 90, wherein the cannula has a bore size of at least 1.16 mm.

* * * * *